(12) United States Patent
Mauch et al.

(10) Patent No.: US 8,177,802 B2
(45) Date of Patent: May 15, 2012

(54) APPARATUS FOR PERCUTANEOUSLY CREATING NATIVE TISSUE VENOUS VALVES

(75) Inventors: Kevin Mauch, Windsor, CA (US); Maria Arreguin, Windsor, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 556 days.

(21) Appl. No.: 12/335,804

(22) Filed: Dec. 16, 2008

(65) Prior Publication Data

US 2010/0152682 A1    Jun. 17, 2010

(51) Int. Cl.
*A61B 17/32* (2006.01)
*A61B 17/22* (2006.01)
*A61M 29/00* (2006.01)
*A61M 29/02* (2006.01)

(52) U.S. Cl. ........ 606/167; 606/191; 606/192; 606/194; 606/159

(58) Field of Classification Search .................. 606/167, 606/170, 191–195, 159, 185, 198; 604/509, 604/95.03, 96.01, 103; 623/1.11, 1.23; 128/898
See application file for complete search history.

(56) References Cited

U.S. PATENT DOCUMENTS

| | | | |
|---|---|---|---|
| 5,902,268 A * | 5/1999 | Saab | 604/96.01 |
| 6,190,353 B1 | 2/2001 | Makower et al. | |
| 6,902,576 B2 | 6/2005 | Drasler et al. | |
| 7,008,411 B1 | 3/2006 | Mandrusov et al. | |
| 2003/0181843 A1 * | 9/2003 | Bibber et al. | 604/8 |
| 2006/0271090 A1 * | 11/2006 | Shaked et al. | 606/192 |

FOREIGN PATENT DOCUMENTS

| | | |
|---|---|---|
| EP | 0611582 | 8/1994 |
| WO | WO95/26776 | 10/1995 |
| WO | WO01/49357 | 7/2001 |

OTHER PUBLICATIONS

Dalsing, Michael, "Prosthetic venous Valves" The Vein Book, Chapter 64, pp. 593-598, 2006.
Peruzzi et al., "A New Autologous Venous Valve by Intimal Flap" Minerva Cardioangiologica, vol. 51, No. 4, p. 395, Aug. 2003.
Maleti et al., "Neovalve Construction in Postthrombotic Syndrome" The Journal of vascular Surgery, vol. 43, No. 4, pp. 794-799.

* cited by examiner

*Primary Examiner* — Amy Lang

(57) ABSTRACT

Percutaneous apparatus for forming a bicuspid venous valve from autologous tissue are disclosed. A multilumen catheter is disclosed that includes a delivery shaft positioned on either side of the balloon. When the balloon is inflated within the vein at a treatment location where a bicuspid valve is to be created, the delivery shafts are pressed into the wall of the vein by the inflated balloon so that exit ports in the delivery shafts are at diametrically opposed locations. The delivery shafts may than be used to deliver puncture elements through the exit ports and into the vessel wall to gain access to a subintimal layer of the vein wall. In this manner, the inventive multilumen catheter aids in making properly positioned flaps of venous tissue for creating a bicuspid venous valve from autologous tissue.

4 Claims, 9 Drawing Sheets

APPARATUS FOR PERCUTANEOUSLY CREATING NATIVE TISSUE VENOUS VALVES

FIELD OF THE INVENTION

The invention relates to apparatus and methods for percutaneously creating a one-way venous valve in vivo from autologous tissue.

BACKGROUND OF THE INVENTION

Venous valves are found within native venous vessels and are used to assist in returning blood back to the heart in an antegrade direction from all parts of the body. The venous system of the leg for example includes the deep venous system and the superficial venous system, both of which are provided with venous valves that are intended to direct blood toward the heart and prevent backflow or retrograde flow, which can lead to blood pooling or stasis in the leg. Incompetent valves can also lead to reflux of blood from the deep venous system to the superficial venous system and the formation of varicose veins. Superficial veins, which include the greater and lesser saphenous veins, have perforating branches in the femoral and popliteal regions of the leg that direct blood flow toward the deep venous system and generally have a venous valve located near the junction with the deep system. Deep veins of the leg include the anterior and posterior tibial veins, popliteal veins, and femoral veins. Deep veins are surrounded in part by musculature tissue that assists in generating flow due to muscle contraction during normal walking or exercising. Veins in the lower leg have a static pressure while standing of approximately 80-90 mm Hg that may reduce during exercise to 60-70 mm Hg. Despite exposure to such pressures, the valves of the leg are very flexible and can close with a pressure drop of less than one mm Hg.

Figure 1A:
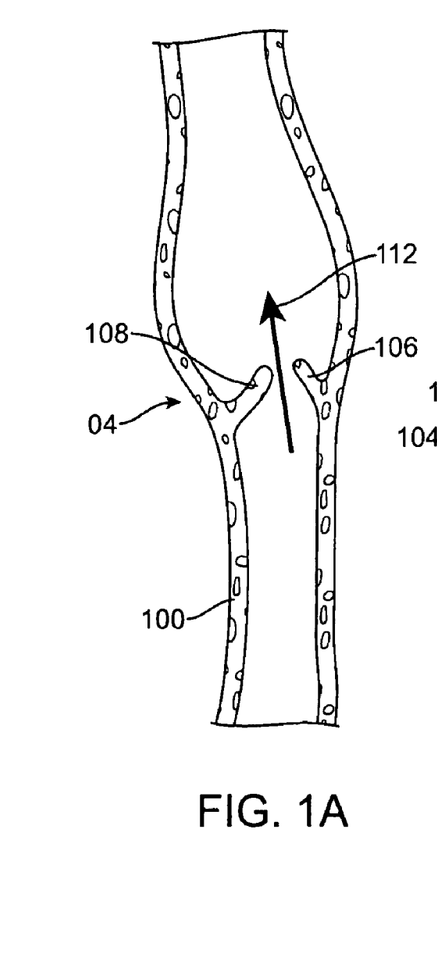
FIGS. 1A-1B are schematic representations of blood flow through a healthy valve within a vein.
Figure 1B:
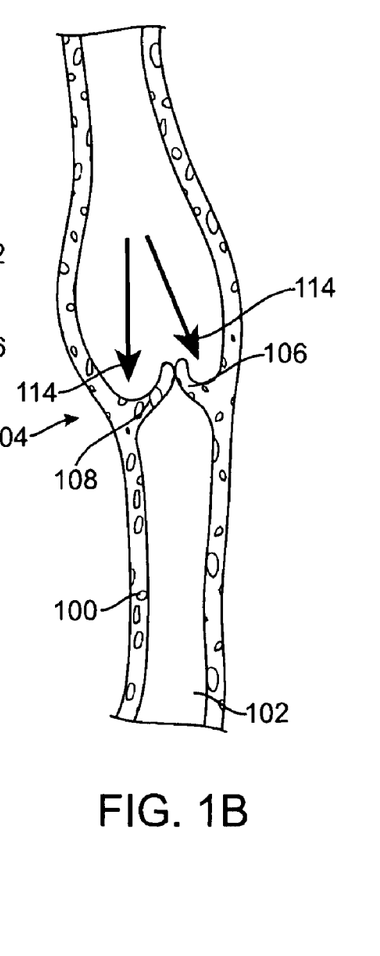

FIGS. 1A-1B are schematic representations of blood flow through a healthy native valve 104 within a vein 100. Venous valve 104 controls blood flow through lumen 102 of vein 100 via leaflets 106, 108. More particularly, venous valve 104 opens to allow antegrade flow 112 through leaflets 106, 108 as shown in FIG. 1A. Venous valve 104 closes to prevent backflow or retrograde flow 114 through leaflets 106, 108 as shown in FIG. 1B.

Veins typically in the leg can become distended from prolonged exposure to excessive pressure and due to weaknesses found in the vessel wall causing the natural venous valves to become incompetent leading to retrograde blood flow in the veins. Such veins no longer function to help pump or direct the blood back to the heart during normal walking or use of the leg muscles. As a result, blood tends to pool in the lower leg and can lead to leg swelling and the formation of deep venous thrombosis and phlebitis. The formation of thrombus in the veins can further impair venous valvular function by causing valvular adherence to the venous wall with possible irreversible loss of venous function. Continued exposure of the venous system to blood pooling and swelling of the surrounding tissue can lead to post phlebitic syndrome with a propensity for open sores, infection, and may lead to possible limb amputation.

Chronic Venous Insufficiency (CVI) occurs in patients that have deep and superficial venous valves of their lower extremities (below their pelvis) that have failed or become incompetent due to congenital valvular abnormalities and/or pathophysiologic disease of their vasculature. As a result, these patients suffer from varicose veins, swelling and pain of the lower extremities, edema, hyper pigmentation, lipodermatosclerosis, and deep vein thrombosis (DVT). Such patients are at increased risk for development of soft tissue necrosis, ulcerations, pulmonary embolism, stroke, heart attack, and amputations.

Figure 2:
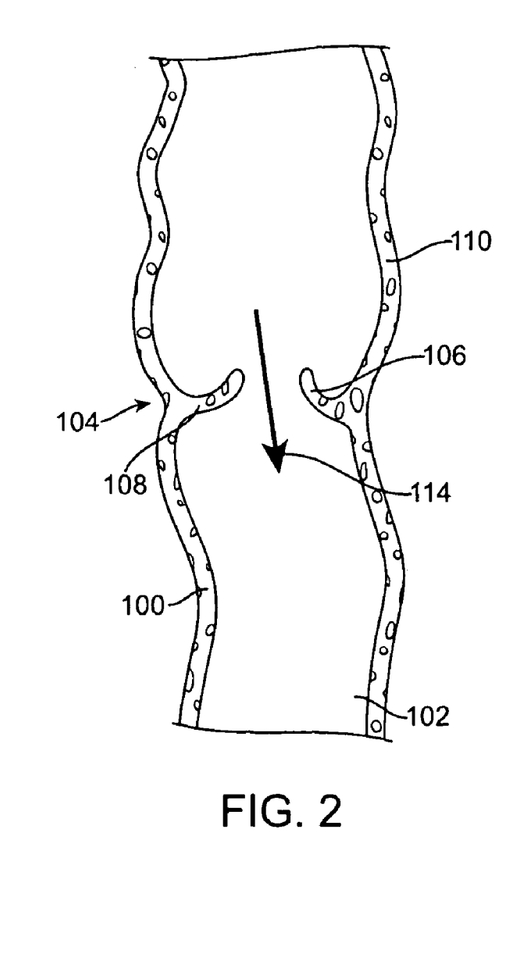
FIG. 2 is a schematic representation of blood flow through an incompetent valve within a vein.

FIG. 2 is a schematic representation of blood flow through an incompetent venous valve. Backflow or antegrade flow 114 leaks through venous valve 104 creating blood build-up that eventually may destroy the venous valve and cause a venous wall bulge 110. More specifically, the vessel wall of vein 100 expands into a pouch or bulge, such that the vessel has a knotted appearance when the pouch is filled with blood. The distended vessel wall area may occur on the outflow side of the valve above leaflets 106, 108 as shown in FIG. 2, and/or on the inflow side of the valve below leaflets 106, 108. After a vein segment becomes incompetent, the vessel wall dilates such that the fluid velocity decreases within the incompetent vein segment, which may lead to flow stasis and thrombus formation in the proximity of the venous valve.

Repair and replacement of venous valves presents a formidable problem due to the low blood flow rate found in native veins, the very thin wall structure of the venous wall and the venous valve, and the ease and frequency of which venous blood flow can be impeded or totally blocked for a period of time. Surgical reconstruction techniques used to address venous valve incompetence include venous valve bypass using a segment of vein with a competent valve, venous transposition to bypass venous blood flow through a neighboring competent valve, and valvuloplasty to repair the valve cusps. These surgical approaches may involve placement of synthetic, allograft and/or xenograft prostheses inside of or around the vein. However, such prostheses have not been devoid of problems leading to thrombus and/or valve failure due to leaflet thickening/stiffening, non-physiologic flow conditions, non-biocompatible materials and/or excessive dilation of the vessels with a subsequent decrease in blood flow rates.

Percutaneous methods for treatment of venous insufficiency are being studied some of which include placement of synthetic, allograft and/or xenograft prosthesis that suffer from similar problems as the surgically implanted ones discussed above.

In addition, venous valve formation from autologous tissue has been disclosed in U.S. Pat. No. 6,902,576 to Drasler et al. Drasler et al. suggests use of autologous tissue with blood contact of an endothelial layer to eliminate biocompatability issues and also alleviate thrombus formation due to low flow. However, methods of in situ venous valve formation according to Drasler et al. are surgical in nature and involve reshaping a distended, diseased vein, which carries with it the risk of rupture or tearing of the thin-walled structure.

In view of the foregoing, there is still a need for methods and apparatus to restore normal venous circulation to patients suffering from venous valve insufficiency, wherein the methods and apparatus may be used in percutaneous, minimally invasive procedures. Further, such percutaneous methods and apparatus should attend to biocompatibility and thrombosis issues that current approaches do not adequately address.

BRIEF SUMMARY OF THE INVENTION

Embodiments hereof are directed to percutaneous apparatus for creating bicuspid venous valves from autologous tissue. In an embodiment, a catheter for creating a bicuspid venous valve from autologous tissue includes an elongate catheter shaft that defines an inflation lumen and proximal portions of first and second delivery lumens from a proximal end to a distal end thereof. An inflatable balloon extends from the distal end of the catheter shaft and has an interior fluidly coupled to the inflation lumen. A first delivery shaft defines a distal portion of the first delivery lumen and includes a first distal port for accessing the first delivery lumen. The first delivery shaft is attached to the distal end of the catheter shaft such that the proximal portion of the first delivery lumen forms a continuous lumen with the distal portion of the first delivery lumen. A second delivery shaft defines a distal portion of the second delivery lumen and includes a second distal port for accessing the second delivery lumen. The second delivery shaft is attached to the distal end of the catheter shaft such that the proximal portion of the second delivery lumen forms a continuous lumen with the distal portion of the second delivery lumen. The first delivery shaft longitudinally extends along one side of the balloon and the second delivery shaft longitudinally extends along the opposite side of the balloon such that the first and second distal ports are positioned adjacent a working length of the balloon approximately 180 degrees apart.

When the catheter according to the aforementioned embodiment is tracked to a treatment site where a new valve is to be created within a vein, inflation of the balloon places the first and second distal ports in apposition with the vessel wall at a first and second position that are separated by approximately 180 degrees, or stated another way are diametrically opposed to one and other. Puncture devices, which may be preloaded or subsequently loaded within the first and second delivery lumens, may than be distally advanced from the first and second distal ports into the vessel wall to create intimal dissections in accordance with various methods described herein. In this manner, the inventive catheter aids in making properly positioned intimal flaps for creating a bicuspid venous valve from autologous tissue.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments hereof are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of blood vessels such as the deep and superficial veins of the leg, the invention may also be used in any other body passageways where it is deemed useful. Furthermore, there is no intention to be bound by any expressed or implied theory presented in the preceding technical field, background, brief summary or the following detailed description.

Figure 3:
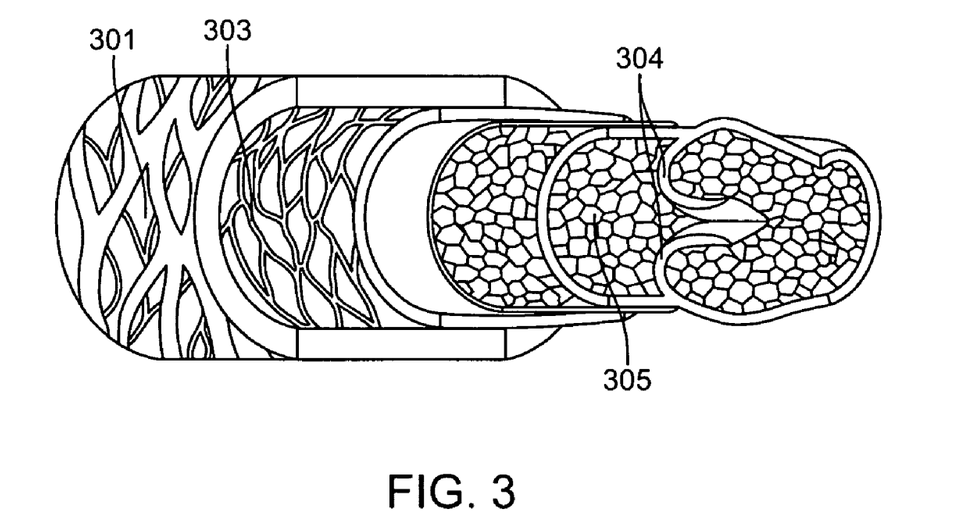
FIG. 3 is a sectional view of the anatomy of a healthy vein and valve thereof.

FIG. 3 depicts a sectional view of the anatomy of a vein wall, which for purposes of this description is shown to consist essentially of an outside layer 301, a middle layer 303 and an inside layer 305. Outside layer 301, called the adventitia, is made of collagen, vasa vasorum and nerve cells. Middle layer 303, or media, is made of smooth muscle cells, where as inside layer 305, or intima, is made up of endothelial cells. The endothelium provide a nonthrombogenic surface for flowing blood. Venous valve 304 having two leaflets is formed from folds of the inner or intimal layer such that both upstream and downstream blood contacting surfaces of valve 304 are covered with endothelium.

Figure 4:
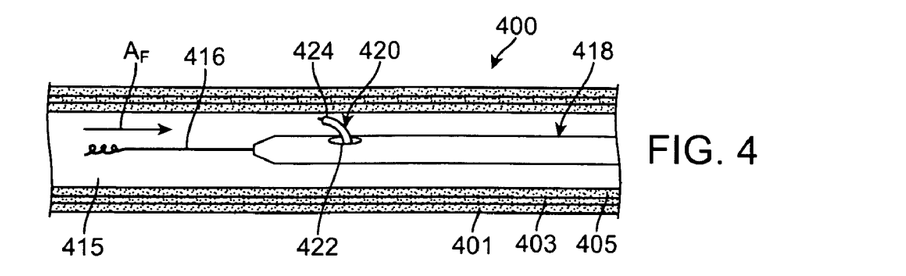
FIGS. 4-6 are schematic representations of a method of forming a venous valve from autologous tissue.
Figure 5:
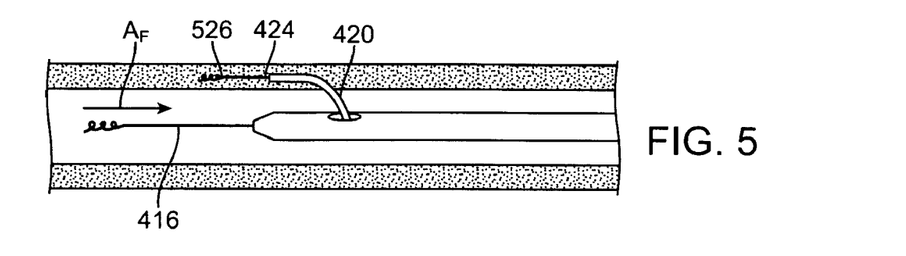
Figure 6:
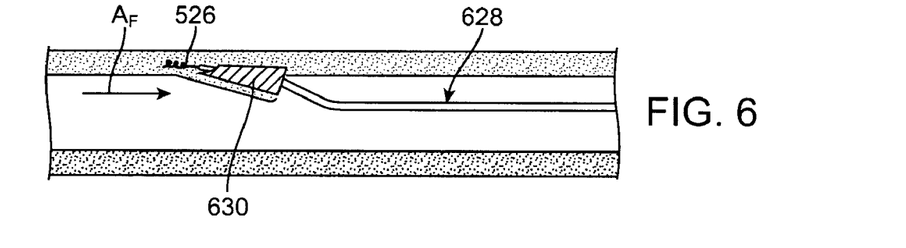

FIGS. 4-6 are schematic representations of a method of forming a venous valve from autologous tissue in accordance with an embodiment hereof, wherein the method includes creating at least one flap in a vein which than acts as a one-way valve in the manner of a native venous valve. Initially luminal access to a desired peripheral vein 400, such as the greater or lesser saphenous, femoral, or popliteal veins, is obtained using standard percutaneous techniques. It should be understood by one of skill in the art that methods as described herein may be used to form an autologous valve in any vein of sufficient thickness to enable a dissection to occur as described in greater detail below. A guidewire 416 is then maneuvered through the vasculature to rest across a target location within lumen 415 of vein 400 where a new vein valve is to be created. A catheter 418 having a deployable puncture element 420 is than advanced over guidewire 416 to the target location. As shown in FIGS. 4 and 5, catheter 418 includes a side exit port 422 for directing puncture element 420 toward a wall of vein 400. Catheters having side exit ports for accommodating a deployable puncture element as well as other catheter designs suitable for use in embodiments hereof, such as passageway-forming catheter device (100) with tissue penetrating element (102) and variations thereof, are shown and described in U.S. Pat. No. 6,190,353 to Makower et al., which is hereby incorporated by reference in its entirety. Additionally, a catheter manufactured by Medtronic, Inc. of Minneapolis, Minn. and sold as a product called the PIONEER Catheter may also be used in performing methods hereof.

Puncture element 420 is distally advanced out of side exit port 422 to puncture or pierce an intimal layer 405 of the wall of vein 400. As shown in FIG. 5, once puncture element 420 is distally advanced, a distal tip 424 thereof is pushed into and through the intimal layer 405 to create a subintimal pathway into the vein wall that substantially parallels a longitudinal axis of vein 400. The subintimal pathway may longitudinally extend between intimal layer 405 and medial layer 403, between medial layer 403 and adventitial layer 401, or within medial layer 403; with care being taken that puncture element 420 does not pass entirely through the wall of vein 400. (Each of layers 401, 403, and 405 of the wall of vein 400 are shown in FIG. 4, but it should be noted that this detail has been removed in subsequent figures for clarity.)

Puncture element 420 may be a hollow needle-like instrument, as shown in FIGS. 4 and 5, having a lumen that permits a second guidewire 526 to be distally advanced into the subintimal pathway. Second guidewire 526 is then distally advanced further within the wall of vein 400 so that tissue of the vein wall is separated to thereby create a dissection plane. In order for guidewire 526 to perform the dissection, a distal end thereof may be sharpened to have a pencil-like point that will more readily slice through the tissue. In an alternate embodiment, puncture element 420 may be a solid puncture wire, such as a sharpened mandrel or small, solid Trocar, that not only makes the initial subintimal pathway into the vein wall but also may be distally advanced to create a dissection plane within the vein wall eliminating the need for a second guidewire.

Fluoroscopic guidance of the advancing second guidewire 526 may be utilized to assure a length of the dissection plane created within the vein wall, as a length of the dissection plane will determine a length of the resulting flap. In order to make a monocuspid flap, the flap must have a free edge length of greater than half of the circumference of the vessel lumen with the depth of the dissection plane being sufficient to allow the resulting flap to touch the opposite side of the vessel wall. In order to make a bicuspid flap, each flap must have a free edge length of roughly half of the circumference of the vessel lumen with the depth of each dissection plane being sufficient enough to allow the resulting flaps to touch one another in the centerline of the vessel lumen. In order to determine an accurate depth/length of the dissection plane, an accurate measurement of the diameter of the vessel may be obtained by using fluoroscopy and quantitative coronary angiography (QCA). In such a procedure, the clinician uses a tool to "mark" the monitor with the fluoroscopic image. It has a calibrated measurement system so the clinician can accurately measure the diameter of the vein.

After the dissection plane is created, catheter 418 and puncture element 420 are proximally retracted and removed while a position of a distal end of second guidewire 526 is maintained within the dissection plane. It should be understood that a remainder of second guidewire 526 proximally extends within the vasculature such that a proximal end thereof (not shown) is available to a clinician outside the patient.

Figure 7A:
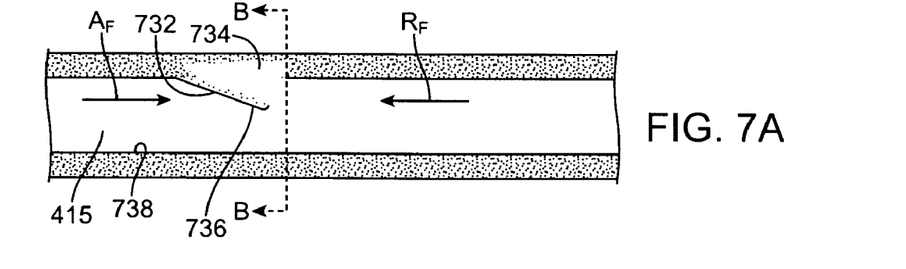
FIG. 7A is a schematic representation of a monocuspid venous valve formed in accordance with embodiments hereof.
Figure 7B:
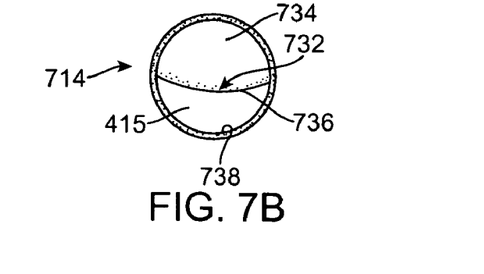
FIG. 7B is a cross-sectional view of FIG. 7A taken along line B-B.

To complete the formation of the new venous valve, a balloon catheter 628 is backloaded onto the proximal end of second guidewire 526 to be tracked thereover until a balloon 630 is positioned within the dissection plane, as shown in FIG. 6. Balloon 630 of balloon catheter 628 is subsequently inflated within the dissection plane to further dissect the intimal and/or medial tissue from the remaining wall tissue and thereby simultaneously form a flap 732 of tissue and a pocket or sinus 734 between flap 732 and the remaining tissue of the vein wall, which are best shown in FIGS. 7A and 7B where balloon catheter 628 is removed. A flap by definition is a moveable piece of tissue partly connected to the body, and accordingly, it should be understood by the preceding description that a distal end of flap 732 remains connected to the remaining tissue of vein 400 while a proximal end or edge of the flap 732 is dissected away from the remaining tissue of the vein wall. Balloon 630 has a tapered shape with a distal inflated diameter that is smaller than a proximal inflated diameter in order to create a conically shaped recess between the dissected flap 732 and the remaining tissue of the vein wall. The conically shaped recess or space defines pocket or sinus 734 and the shape, which mimics a native valve sinus, aids in permitting blood to fill pocket 734 and close flap 732.

In the embodiment of FIGS. 7A and 7B, flap 732 includes a free edge 736 of a sufficient length to make contact with an opposing wall 738 of lumen 415, such that in the absence of antegrade blood flow, represented by arrow $A_F$, free edge 736 seals against opposing wall 738 while retrograde or gravitational blood flow, represented by arrow $R_F$, fills pocket 734. When antegrade blood flow $A_F$ is once again present in vein 400, flap 732 is pushed away from opposing wall 738, as shown in FIG. 7B, to allow blood flow through venous valve 714 on its way back to the heart. In such an embodiment, flap 732 and pocket 734 constitute a one-way monocuspid or one-leaflet venous valve 714 of autologous tissue.

Figure 7C:
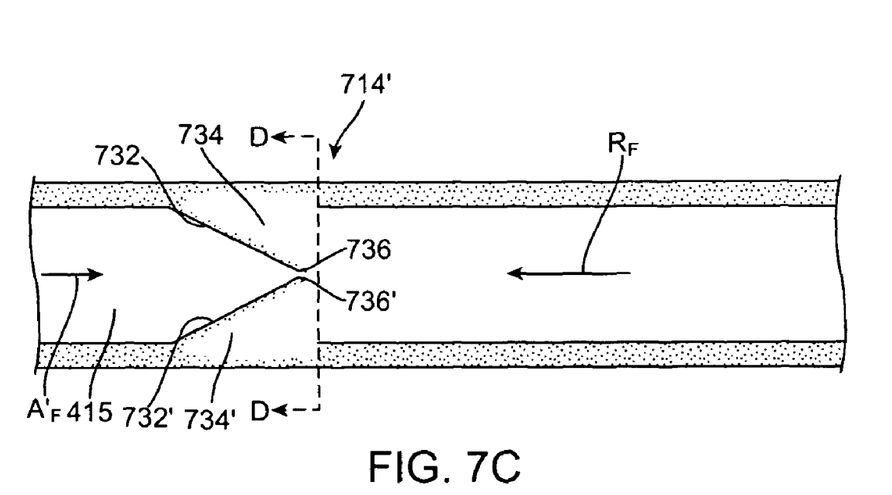
FIG. 7C is a schematic representation of a bicuspid venous valve formed in accordance with embodiments hereof.
Figure 7D:
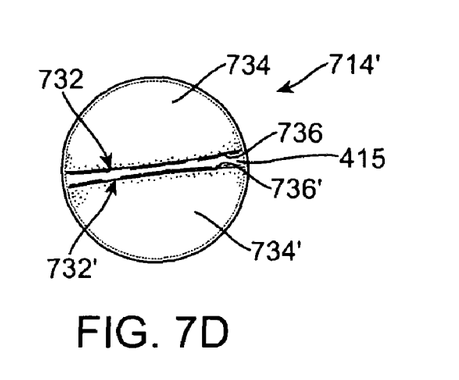
FIG. 7D is a cross-sectional view of FIG. 7C taken along line D-D.

In another embodiment hereof, the method of creating a flap and pocket as described above may be repeated at an opposed location within the vein, or approximately 180 degrees away from where first flap 732 and pocket 734 have been made, in order to form a second flap 732' and a second pocket 734' as shown in FIGS. 7C and 7D. Such an embodiment forms a bicuspid or two-leaflet venous valve 714' where free edges 736, 736' meet to close lumen 415 in the absence of antegrade blood flow $A_F$ when retrograde blood flow $R_F$ fills pockets 734, 734'. In another embodiment (not shown), the method of creating a flap and pocket may be performed three times to form a tricuspid or three-leaflet valve.

In each of the aforementioned embodiment, the dissected flaps 732, 732' provide the same internal, i.e., facing the blood flow, tissue structure as a native valve thus providing a distinct advantage over prosthetic valve approaches. If the newly created flaps or leaflets 732, 732' do not exhibit enough structural integrity to take the shape of a cusp or leaflet or if the flaps remain adhered to the remaining tissue of the vein wall the performance of those structures may be supplemented via biasing elements placed into pockets 734, 734'. The biasing elements are designed to hold a shape of the pockets and do not offer much resistance to antegrade blood flow but instead collapse and allow the valve to open in the presences of antegrade flow as will be discussed in more detail below with reference to FIGS. 14, 14A and 14B.

Other embodiments hereof include multilumen catheter systems for simultaneously creating directly opposing flaps and corresponding pockets/sinuses in the venous wall by utilizing subintimal dissection techniques. Since many venous valves have two cusps, flaps or leaflets that come together to prevent the back flow of blood through the vein, multilumen catheters allowing both flaps to be created at the same time are an improvement over the previously described methods that require making the flaps one at a time.

Figure 8:
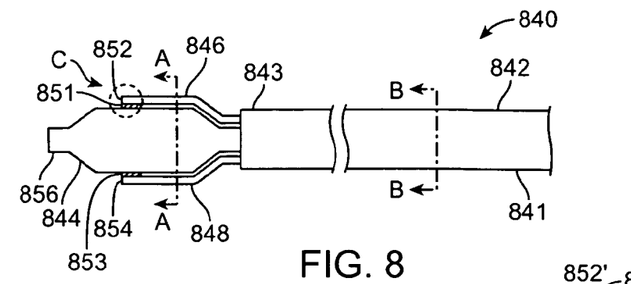
FIG. 8 is a side view of a catheter in accordance with an embodiment hereof.
Figure 8A:
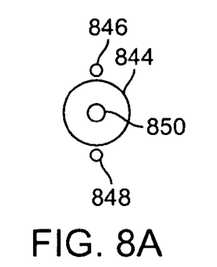
FIG. 8A is a cross-sectional view of the catheter of FIG. 8 taken along line A-A.
Figure 8B:
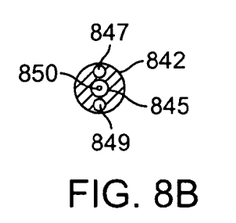
FIG. 8B is a cross-sectional view of the catheter of FIG. 8 taken along line B-B.
Figure 8C:
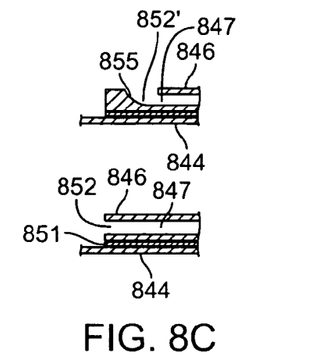
FIG. 8C depicts sectional views of alternate embodiments of the catheter of FIG. 8 within area C.

FIG. 8 depicts a multilumen catheter 840 according to an embodiment hereof, with FIGS. 8A, 8B, and 8C showing various sectional views thereof. Multilumen catheter 840 includes an elongate catheter shaft 842 with a proximal end 841 and a distal end 843. Catheter shaft 842 defines an inflation lumen 845 and proximal portions of first and second delivery lumens 847, 849. A balloon 844, shown inflated in FIG. 8, distally extends from and is fluidly coupled to distal end 843 of catheter shaft 842, such that an interior of balloon 844 is in fluid communication with inflation lumen 845. Similarly, first and second delivery shafts 846, 848, which respectively define distal portions of first and second delivery lumens 847, 849, extend from and are attached to distal end 843 of catheter shaft 842, such that the proximal and distal portions of first and second delivery lumens 847, 849 form continuous lumens. Catheters according to embodiments hereof may be made from any suitable material known to one of skill in the art of catheter construction, including by example, polyethylene, Polyimide, PEBAX, nylon, co-polyester elastomer, and PEEK.

As shown in FIGS. 8 and 8A, first delivery shaft 846 has a first distal port 852 that is positioned on one side of balloon 844 and second delivery shaft 848 has a second distal port 854 that is positioned on the other side of balloon 844 approximately 180° from first distal port 852. First and second delivery shafts 846, 848 are detached from balloon 844 except at bonds 851, 853, which are made proximate first and second distal ports 852, 854. In such a configuration, semi-detached first and second delivery shafts 846, 848 do not interfere with the inflation of balloon 844. In an alternate embodiment, first and second delivery shafts 846, 848 may be attached along their length to the balloon working length.

FIG. 8C depicts alternate sectional views of area C in FIG. 8, wherein each sectional view represents an embodiment of multilumen catheter 840. Each of the sectional views shows the distal end of first delivery shaft 846 being attached by bond 851 to balloon 844. However, in one sectional view first distal port 852 opens in an end surface of first delivery shaft 846, whereas in the other sectional view first distal port 852' opens in a side surface of first delivery shaft 846 and includes a ramp 855 for directing instruments delivered through first delivery lumen 847 toward a vein wall in vivo.

In the embodiment of FIG. 8B, catheter shaft 842 is a polymeric extrusion with inflation lumen 845 and first and second delivery lumens 847, 849 formed therein during the extrusion process. A guidewire shaft 850 defining a guidewire lumen extends within inflation lumen 845 of catheter shaft 842 through an interior of balloon 844 to a distal tip 856. It would be understood by one skilled in the art of catheter design that there are numerous ways to produce catheter shaft 842 having an inflation lumen, two delivery lumens and a guidewire lumen without departing from the scope of the present invention.

Figure 9:
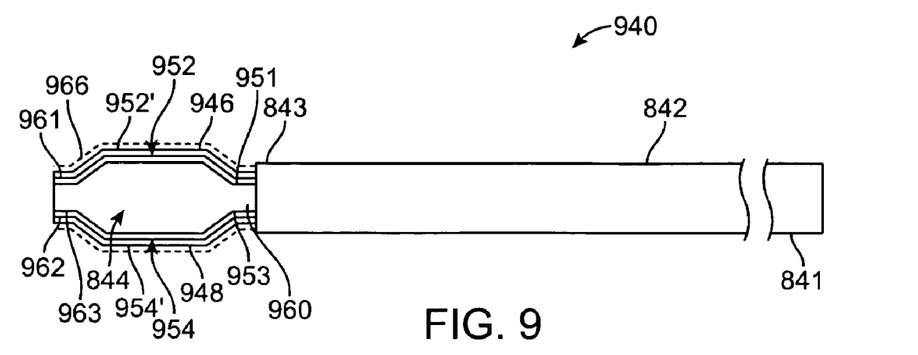
FIG. 9 is a side view of a catheter in accordance with another embodiment hereof.

FIG. 9 depicts a multilumen catheter 940 according to another embodiment hereof. Multilumen catheter 940 is of similar construction to multilumen catheter 840 and for convenience where the structure is the same as that previously described with reference to multilumen catheter 840 in FIG. 8 it bears the same reference numbers in FIG. 9 and will not be further described here. Similar to the embodiment of FIG. 8, first and second delivery shafts 946, 948, which respectively define distal portions of first and second delivery lumens 847, 849, extend from and are attached to distal end 843 of catheter shaft 842, such that the proximal and distal portions of first and second delivery lumens 847, 849 form continuous lumens. However, in the embodiment of FIG. 9, first and second delivery shafts 946, 948 extend from a proximal end 960 of balloon 844 to a distal end 962 of balloon 844. A first distal port 952 is disposed in a sidewall of first delivery shaft 946 and is radially positioned on one side of balloon 844 and a second distal port 954 is disposed in a sidewall of second delivery shaft 948 and is radially positioned on the other side of balloon 844 approximately 180° from first distal port 952. In an embodiment, first and second distal ports 952, 954 are longitudinally positioned at approximately the midpoint of the working length of balloon 844. Each of first and second distal ports 952, 954 open so that when multilumen catheter 940 is placed within a vessel lumen each port faces an opposed surface of the vessel wall. In another embodiment, a ramp, such as ramp 855 of FIG. 8C, may be made within first and second delivery lumens 847, 849 proximate first and second distal ports 952, 954 for directing instruments delivered through first and second delivery lumens 847, 849 toward the vein wall in vivo.

First and second delivery shafts 946, 948 are detached from balloon 844 except at first bonds 951, 953 at the balloon proximal end 960 and second bonds 961, 963 at the balloon distal end 962. In various embodiments, the first and second bonds may be made by an adhesive or by creating a thermal bond between the materials of the components with, by e.g., heat shrink tubing. In such a configuration, semi-detached first and second delivery shafts 946, 948 do not interfere with the inflation of balloon 844. Shown in outline in FIG. 9 is an optional stretchable sheath 966 that holds the detached portions of first and second delivery shafts 946, 948 in apposition with balloon 844 during tracking of multilumen catheter 940 through the vasculature but that also allows for inflation of balloon 844 at the treatment site without being removed. Sheath 966 has first and second side openings 952', 954' that correspond with first and second distal ports 952, 954 to allow egress of medical instruments from first and second delivery lumens 847, 849 via the ports. In an embodiment, sheath 966 may be of polyurethane or another elastomeric material and may be attached to the balloon by either a friction fit, with an adhesive, or thermal bonding the ends. Multilumen catheter 940 is used to create a new bicuspid venous valve of autologous tissue in a vein in a manner to be described below with reference to FIGS. 10-14 and the multilumen catheter of FIG. 8.

With reference to FIGS. 10-14, a method of creating a bicuspid venous valve of autologous tissue utilizing multilumen catheter 840 will now be described. Lumenal access to the venous vasculature is obtained using standard percutaneous techniques. A guidewire 1016 is maneuvered to a treatment site within vein 1000 where a new bicuspid valve is to be created. Multilumen catheter 840 with balloon 844 in a deflated, low-profile configuration (not shown) is tracked over guidewire 1016 through the vasculature to the treatment site.

Figure 10:
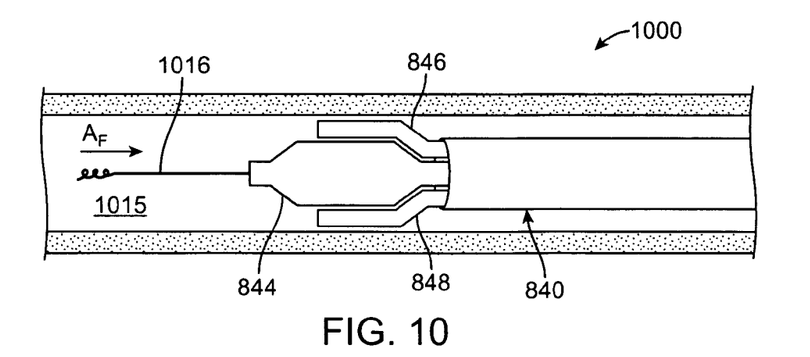
FIGS. 10-13 are schematic representations of a method of forming a venous valve from autologous tissue in accordance with another embodiment hereof.
Figure 11:
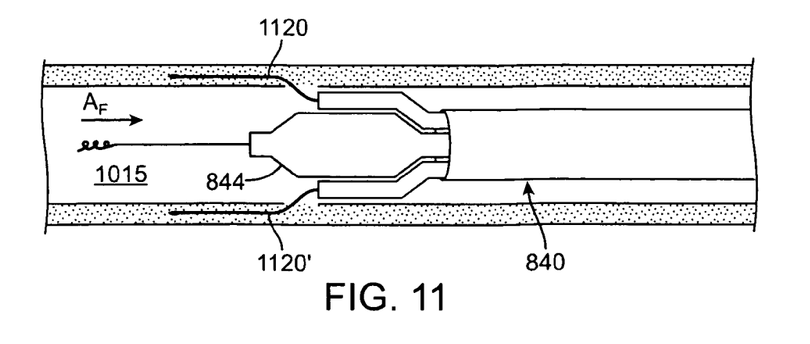

Next, first and second puncture wires 1120, 1120' are simultaneously or contemporaneously backloaded into respective proximal ends (not shown) of first and second delivery lumens 847, 849. In various embodiments, puncture wires 1120, 1120' may be formed from needles or guidewire proximal portions of approximately 0.014" in diameter that have sharpened distal ends. Puncture wires 1120, 1120' are advanced through first and second delivery lumens 847, 849 until distal ends thereof are positioned within the lumens just proximate of first and second distal ports 852, 854, respectively. In another embodiment, puncture wires 1120, 1120' may be preloaded within first and second delivery lumens 847, 849 prior to tracking catheter 840 to the treatment site. Balloon 844 is than inflated via inflation fluid supplied through the inflation lumen of multilumen catheter 840. It would be understood by one skilled in the art of making catheters that a hub or other adapter would be attached to proximal end 841 of multilumen catheter 840 to connect a supply of inflation fluid for use in expanding balloon 844. The inflation of balloon 844 presses first and second delivery shafts 846, 848 into apposition with the interior surface of the vein wall.

Figure 12:
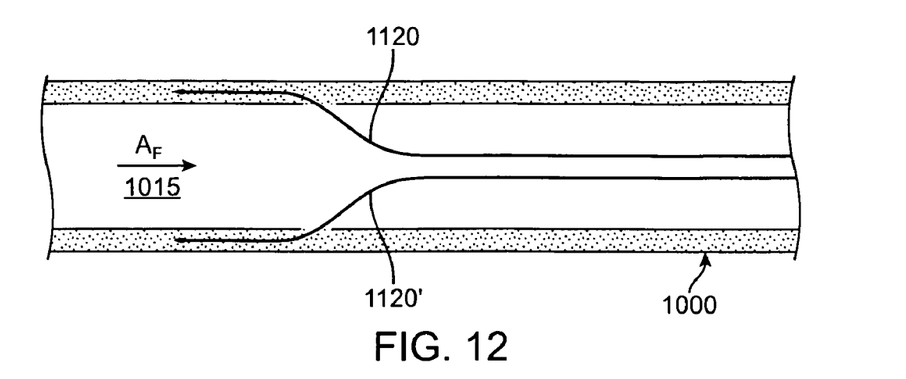

Puncture wires 1120, 1120' are than pushed further distally to exit first and second distal ports 852, 854, respectively, to penetrate into the vein wall and thereby creating opposing subintimal pathways. Puncture wires 1120, 1120' are subsequently distally advanced further into the subintimal space an appropriate length to create opposing dissection planes in the vein wall, as shown in FIG. 11. The distance puncture wires 1120, 1120' extend within the dissection plane may be observed fluoroscopically and should be at least as long as half the vessel diameter to achieve a mid-line meeting or coaptation of the created valves. With puncture wires 1120, 1120' maintained in place within the subintimal space, balloon 844 may be deflated and multilumen catheter 840 removed from the patient's body, as shown in FIG. 12.

Figure 13:
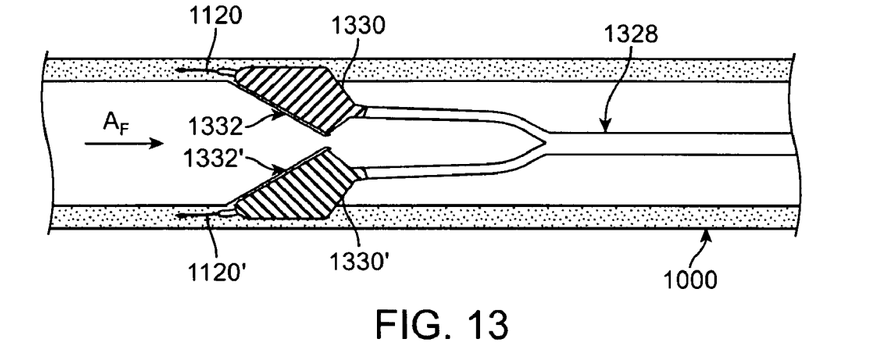
Figure 14:
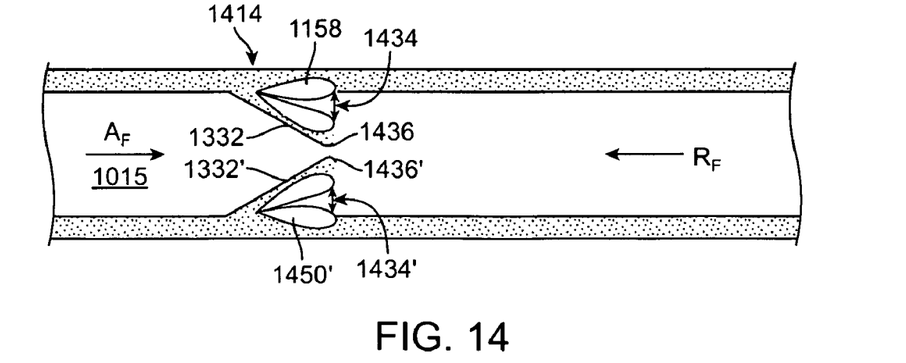
FIG. 14 is a schematic representation of a bicuspid venous valve formed in accordance with embodiments hereof.

Next, a dual balloon catheter 1328 having a first balloon 1330 and a second balloon 1330' is advanced over puncture wires 1120, 1120' until the respective balloons 1330, 1330' are properly positioned within the respective dissection planes made in the wall of vein 1000. Balloons 1330, 1330' are simultaneously inflated within their respective dissection planes to create first and second flaps 1332, 1332' and first and second pockets/sinuses 1434, 1434', as shown in FIGS. 13-14. Balloons 1330, 1330' are than deflated and dual balloon catheter 1328 is removed from the vessel. In another embodiment hereof, first and second balloon catheters may be used in performing this step of the intimal dissection instead of dual balloon catheter 1320.

In an embodiment, first and second balloons 1330, 1330' have tapered shapes with a distal inflated diameter that is smaller than a proximal inflated diameter. The tapered shape of balloons 1330, 1330' create conically shaped recesses between the dissected first and second flaps 1332, 1332' and the respective remaining medial tissue. The conically shaped recesses or spaces define first and second pockets or sinuses 1434, 1434' and their shape, which mimics native valve sinuses, aids in permitting blood to fill first and second pockets 1434, 1434' and close first and second flaps 1332, 1332'. An expanded proximal diameter of balloons 1330, 1330' may be selected such that the resulting flaps 1332, 1332', and particularly a length of free edges 1436, 1436', are able to contact each other within the lumen in the absence of antegrade blood flow $A_F$ thus forming a new one-way valve 1414 in the vessel.

Accordingly, new venous valve 1414 formed in accordance with this embodiment operates as a bicuspid or two-leaflet venous valve where first and second free edges 1436, 1436' meet to close lumen 1015 in the absence of antegrade blood flow $A_F$ when retrograde blood flow $R_F$ fills first and second pockets 1434, 1434'. The dissected first and second flaps 1432, 1432' provide the same internal, i.e., facing the blood flow, tissue structure as a native valve thus providing a distinct advantage over prosthetic valve approaches.

Figure 14A:
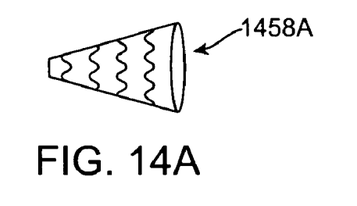
FIG. 14A is a schematic representation of a tapered stent for use in venous valves formed in accordance with embodiments hereof.
Figure 14B:
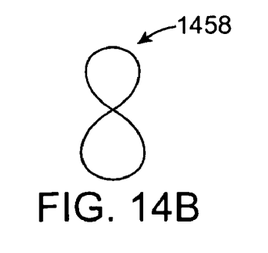
FIG. 14B is a schematic representation of a biasing element for use in venous valves formed in accordance with embodiments hereof.

In order to increase the structural integrity of first and second flaps 1332, 1332', optional biasing elements, such as spring clip devices 1458, 1458' shown in FIG. 14, may be placed into first and second pockets 1434, 1434' to aid in completely closing lumen 1015 in the absence of antegrade blood flow $A_F$ by biasing first and second flaps 1332, 1332' against one and other. In this manner, retrograde blood flow $R_F$ is impeded from seeping through free edges 1436, 1436' and causing reflux to instead fill first and second pockets 1434, 1434'. When antegrade blood flow $A_F$ once again pushes upon first and second flaps 1332, 1332', spring clip devices 1458, 1458' are compliant enough to compress to allow first and second flaps 1332, 1332' to part such that antegrade blood flows through bicuspid valve 1414. Spring clip devices 1458, 1458' would be percutaneously delivered. In an embodiment the spring clips may be manufactured from a superelastic material such as nitinol. The clips may be shaped into a FIG. 8, as shown in FIG. 14B, and then folded at the mid-point to an appropriate angle, as shown in FIG. 14. In an embodiment, a suitable range for this angle is between 20 to 60 degrees. The spring-clip may be shape-set into this configuration using an oven set to an appropriate temperature for the material, by e.g., 525° C. for nitinol. The spring clip would then be loaded into a catheter assembly at the distal tip and advanced to the tissue pockets (sinus). A pusher rod may or other delivery mechanism may then be used to push the spring-clip out of the distal tip of the catheter and into the tissue pocket. Because of the materials superelasticity, the spring clip will self-expand to its original folded FIG. 8 configuration. Thus the material would contact the inner edge of the vessel wall and the inner edge of the created tissue pocket. In another embodiment, a tapered compliant stent 1458A as shown in FIG. 14A may be placed in each of first and second pockets 1434, 1434' to function in the same manner as previously described for spring clip devices 1458, 1458'. Compliant stent 1458A may be made of nitinol with a very thin wall, such as having a wall thickness of between 0.001 to 0.005 inches.

Figure 15:
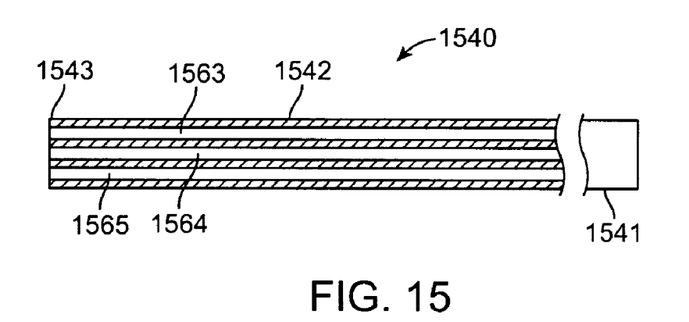
FIG. 15 is a sectional view of a tri-lumen catheter in accordance with another embodiment hereof.

FIG. 15 depicts a multilumen delivery catheter 1540 according to another embodiment hereof for use in a method of simultaneously creating directly opposing flaps and corresponding pockets/sinuses in the venous wall by utilizing subintimal dissection techniques as described in previous embodiments. Delivery catheter 1540 includes an elongate catheter shaft 1542 with a proximal end 1541 and a distal end 1543. Catheter shaft 1542 defines a central delivery lumen 1564 and first and second outer delivery lumens 1563, 1565. In an embodiment, central delivery lumen 1564 may have a greater inner diameter than each of first and second outer delivery lumens 1563, 1565 in order to accommodate delivery of medical devices having larger profiles. In various embodiments, catheter shaft 1542 may be an extruded shaft having an oval, circular or asymmetrically shaped cross-sectional profile. Catheters according to embodiments hereof may be made from any suitable material known to one of skill in the art of catheter construction, including by example, polyethylene, PEBAX, nylon, Polyimide, and PEEK.

Figure 16:
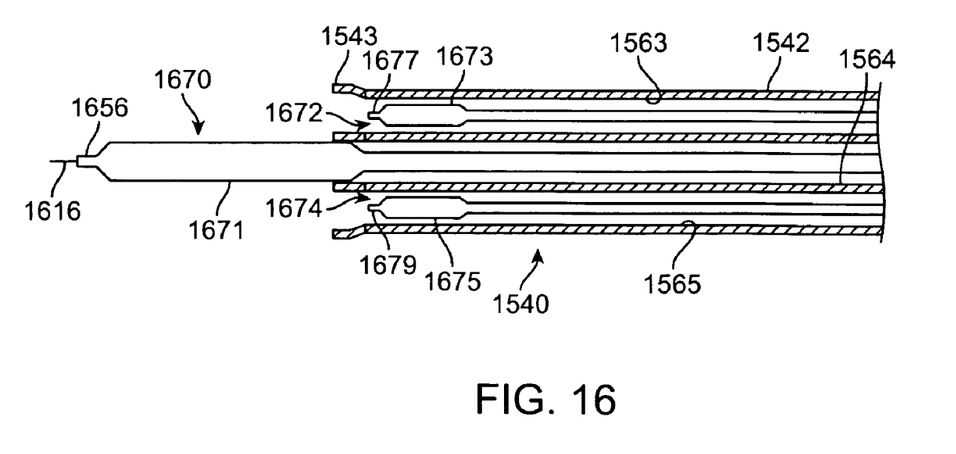
FIGS. 16-21 are schematic representations of a method of forming a venous valve from autologous tissue in accordance with another embodiment hereof.

With reference to FIGS. 16-21, a method of creating a bicuspid venous valve of autologous tissue utilizing delivery catheter 1540 will now be described. FIG. 16 depicts delivery catheter 1540 preloaded in a delivery configuration with a balloon catheter 1670 loaded within central delivery lumen 1564, first tapered balloon catheter 1672 loaded within first outer delivery lumen 1563 and second tapered balloon catheter 1674 loaded within second outer delivery lumen 1565.

Centering balloon 1671 of balloon catheter 1670 distally extends from distal end 1543 of delivery catheter shaft 1542, whereas first and second tapered balloons 1673, 1675 of first and second tapered balloon catheters 1672, 1674 extend for the full-lengths of first and second outer delivery lumens 1563, 1565, respectively, such that distal ends 1677, 1679 of each is positioned proximal of and within the distal end 1543 of catheter shaft 1542. Guidewire 1616 is than preloaded within balloon catheter 1670 such that a distal end of guidewire 1616 extends beyond a distal tip 1656 of balloon catheter 1670. In a similar manner, first and second puncture wires 1820, 1820' are preloaded within first and second tapered balloon catheters 1672, 1674, respectively, such that a distal end of each puncture wire does not extend beyond a respective distal end 1677, 1679 of first and second tapered balloons 1673, 1675.

Figure 17:
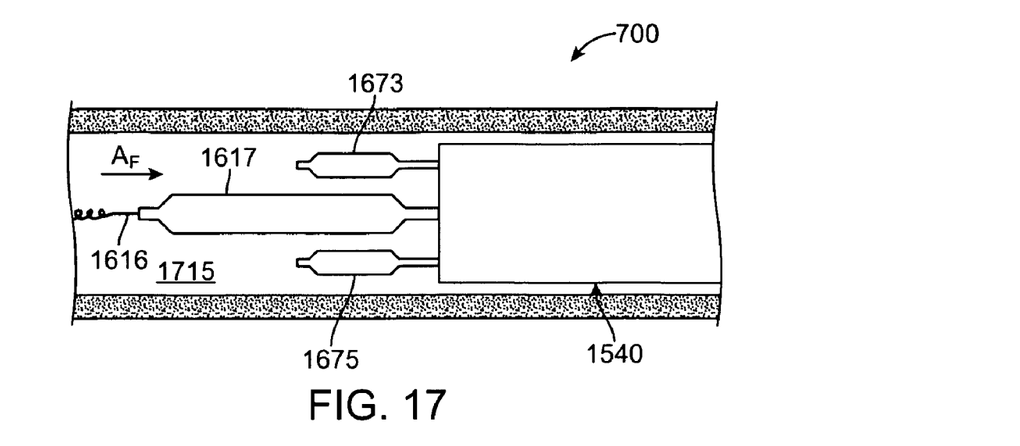

As in the methods described above, lumenal access to the venous vasculature is obtained using standard percutaneous techniques. Guidewire 1616 is distally advanced from balloon catheter 1670 to be maneuvered to a treatment site within vein 1700 where a new bicuspid valve is to be created. Delivery catheter 1540 with centering balloon 1671 in a deflated, low-profile configuration is tracked over guidewire 1616 through the vasculature to the treatment site. At the treatment site, first and second tapered balloons 1673, 1675 are distally advanced out of first and second outer delivery lumens 1563, 1565 until each is positioned on an opposite side of centering balloon 1671 along a working length thereof, as best shown in FIG. 17.

Centering balloon 1671 is than inflated via inflation fluid supplied through an inflation lumen of balloon catheter 1670. The inflation of centering balloon 1671 presses first and second tapered balloons 1673, 1675 into apposition with the interior surface of the vein wall and provides a proper angle of approach for directing puncture wires 1820, 1820' into the vessel wall. In another embodiment centering balloon 1671 may be tapered proximally along its working length such that a distal diameter is bigger than a proximal diameter to provide an appropriate angle of approach for the tapered balloons.

Figure 18:
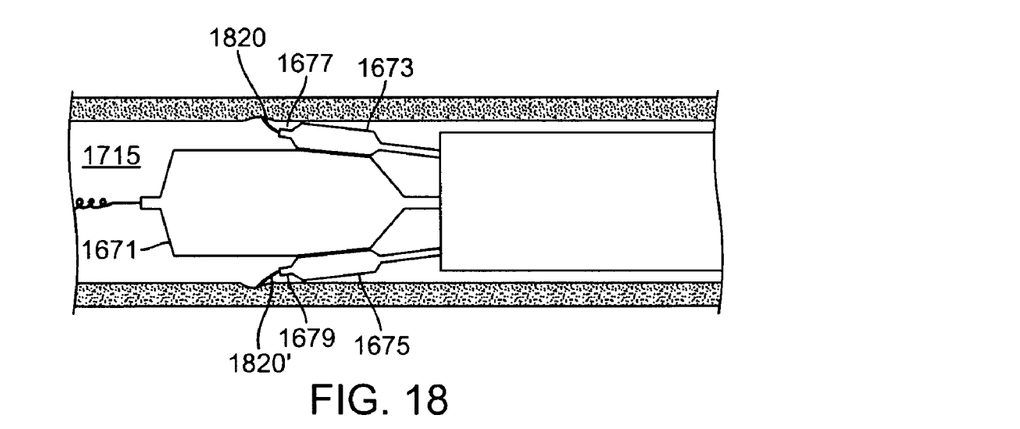
Figure 19:
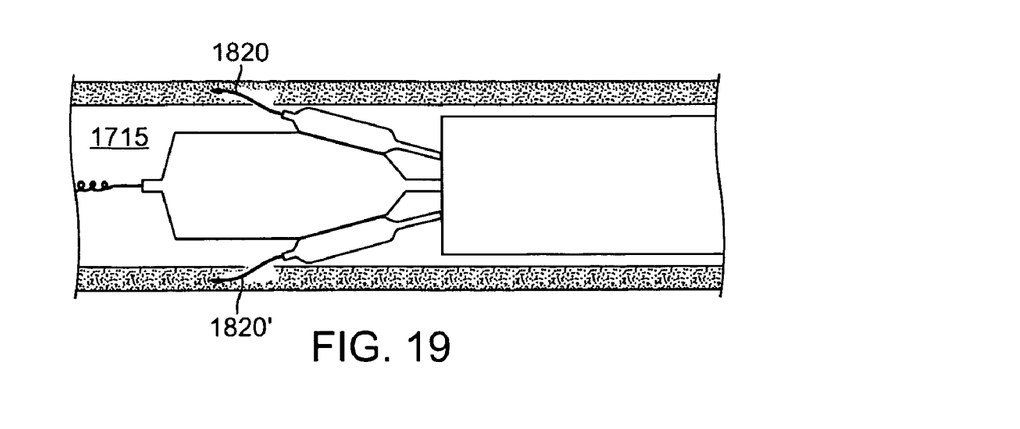
Figure 20:
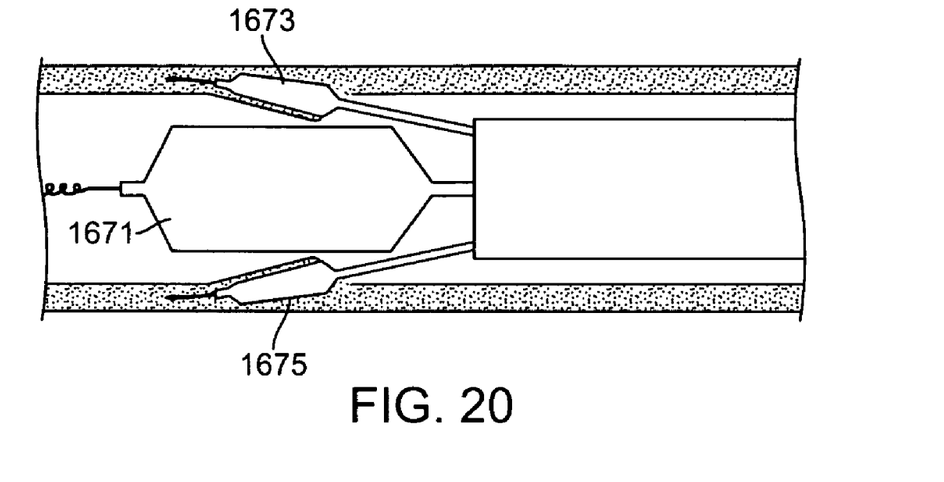
Figure 21:
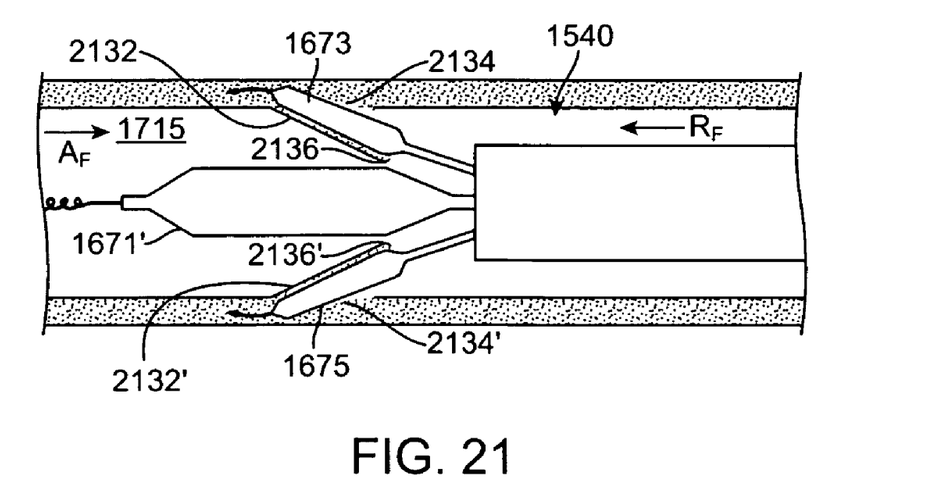

As shown in FIG. 18, first puncture wire 1820 is distally advanced from distal end 1677 of first tapered balloon 1673 to penetrate into the vein wall and thereby creating a first subintimal pathway and second puncture wire 1820' is distally advanced from distal end 1679 of second tapered balloon 1675 to penetrate into the vein wall and thereby creating a second subintimal pathway. Puncture wires 1820, 1820' are subsequently distally advanced further into the subintimal space an appropriate length to create first and second dissection planes in the vein wall, as shown in FIG. 19. In an embodiment, puncture wires 1820, 1820' are distally pushed or advanced simultaneously in order to concurrently form the subintimal pathways and/or the dissection planes. With first and second puncture wires 1820, 1820' maintained in place within the subintimal space, centering balloon 1671 may be slightly deflated to allow first and second tapered balloons 1673, 1675 to be advanced within the first and second dissection planes, respectively, as shown in FIG. 20. Centering balloon 1671 may be slightly deflated again to allow first and second tapered balloons 1673, 1675 to be fully inflated within the first and second dissection planes, respectively, as shown in FIG. 21, to create first and second flaps 2132, 2132' and first and second pockets/sinuses 2134, 2134'. In an embodiment, first and second tapered balloons 1673, 1675 are simultaneously inflated in order to concurrently form the first and second flaps 2132, 2132' and corresponding first and second pockets/sinuses 2134, 2134', as simultaneous inflation may result in more uniform creation of the tissue flaps to assure alignment from one another. Centering balloon 1671 and first and second tapered balloons 1673, 1675 are than fully deflated so that delivery catheter 1540 may be removed from the vessel.

Accordingly, a new venous valve is formed in accordance with the apparatus and method depicted in FIGS. 15-21 that operates as a bicuspid or two-leaflet venous valve where first and second free edges 2136, 2136' meet to close lumen 1715 in the absence of antegrade blood flow $A_F$ when retrograde flow $R_F$ fills first and second pockets 2134, 2134'. As in previous embodiments, the dissected first and second flaps 2132, 2132' provide the same internal, i.e., facing the blood flow, tissue structure as a native valve.

While various embodiments hereof have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope hereof should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A catheter for creating a bicuspid venous valve from autologous tissue, the catheter comprising:

an elongate catheter shaft having a proximal end and a distal end and defining an inflation lumen and proximal portions of first and second delivery lumens;

a balloon extending from the distal end of the catheter shaft and having an interior fluidly coupled to the inflation lumen;

a first delivery shaft defining a distal portion of the first delivery lumen with a first distal port for accessing the first delivery lumen, the first delivery shaft being coupled to the distal end of the catheter shaft such that the proximal portion of the first delivery lumen is connected to the distal portion of the first delivery lumen, wherein a proximal end of the first delivery shaft is directly attached to a proximal end of the balloon and a distal end of the first delivery shaft is directly attached to a distal end of the balloon such that a first delivery shaft portion extending between the attached proximal and distal ends thereof is detached from the balloon and wherein the first distal port is an opening in a sidewall proximal of the distal end of the first delivery shaft; and a second delivery shaft defining a distal portion of the second delivery lumen with a second distal port for accessing the second delivery lumen, the second delivery shaft being coupled to the distal end of the catheter shaft such that the proximal portion of the second delivery lumen is connected to the distal portion of the second delivery lumen, wherein a proximal end of the second delivery shaft is directly attached to the proximal end of the balloon and a distal end of the second delivery shaft is directly attached to the distal end of the balloon such that a second delivery shaft portion extending between the attached proximal and distal ends thereof is detached from the balloon and wherein the second distal port is an opening in a sidewall proximal of the distal end of the second delivery shaft, wherein the first delivery shaft longitudinally extends along one side of the balloon and the second delivery shaft longitudinally extends along the opposite side of the balloon such that the first and second distal ports are positioned on a working length of the balloon approximately 180 degrees apart.

2. The catheter of claim 1, further comprising:

a first puncture device positioned within the first delivery lumen with a distal end of the first puncture device being located adjacent the first distal port; and a second puncture device positioned within the second delivery lumen with a distal end of the second puncture device located adjacent the second distal port.

3. The catheter of claim 2, wherein the first and second puncture devices are selected from a group consisting of guidewires with sharpened distal tips, needles, sharpened mandrels, and mini trocars.

4. The catheter of claim 1, wherein the first and second delivery shafts are made from polyethylene tubing.

* * * * *